United States Patent
Dohmen et al.

(10) Patent No.: US 11,083,901 B2
(45) Date of Patent: Aug. 10, 2021

(54) ELECTRODE FIXING SLEEVE WITH VISUAL FORCE INDICATOR

(71) Applicant: BIOTRONIK SE & Co. KG, Berlin (DE)

(72) Inventors: Daniel Dohmen, Berlin (DE); Alexander Borck, Heidesee (DE); Gernot Kolberg, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 196 days.

(21) Appl. No.: 16/416,514

(22) Filed: May 20, 2019

(65) Prior Publication Data

US 2019/0358462 A1  Nov. 28, 2019

(30) Foreign Application Priority Data

May 25, 2018  (DE) .................... 10 2018 112 560.7

(51) Int. Cl.
*A61N 1/375* (2006.01)
*A61B 17/34* (2006.01)
(Continued)

(52) U.S. Cl.
CPC ...... *A61N 1/37518* (2017.08); *A61B 17/3468* (2013.01); *A61L 31/06* (2013.01);
(Continued)

(58) Field of Classification Search
CPC ............ A61N 2001/058; A61N 1/0551; A61N 1/37518; A61N 2001/0578
See application file for complete search history.

(56) References Cited

U.S. PATENT DOCUMENTS

| 5,152,298 A | 10/1992 | Kreyenhagen et al. |
| 5,603,730 A | 2/1997 | Romkee |

(Continued)

FOREIGN PATENT DOCUMENTS

| DE | 102005016364 B3 | 11/2006 |
| DE | 102016112179 A1 | 1/2018 |
| WO | 2015048777 A1 | 4/2015 |

OTHER PUBLICATIONS

"Involvement of surface-adsorbed water in photochromism of spiropyran molecules deposited on NaY zeolite" by Kevin D. Dubois, Chao Liu, Gonghu Li; Chemical Physics Letters 598 (2014) 53-57; journal homepage: www.elsevier.com/locate/cplett.

(Continued)

*Primary Examiner* — Lynsey C Eiseman
*Assistant Examiner* — Jessica L Mullins
(74) *Attorney, Agent, or Firm* — Buchanan Ingersoll & Rooney PC

(57) ABSTRACT

A fixing device for fixing a longitudinally extended element, having a fixing sleeve that surrounds a lumen extended in an axial direction for receiving the longitudinally extended element, the fixing sleeve having an inner side defining the lumen and an outer side facing away from the inner side, the fixing sleeve being embodied for fixing the fixing sleeve on the longitudinally extended element to be subjected to compression in the radial direction of the fixing sleeve by means of the at least one fixing element. The fixing device has an indicator device that is embodied to visually indicate when a force applied to the fixing sleeve by means of the at least one fixing element for compressing the fixing sleeve attains or exceeds a threshold.

16 Claims, 5 Drawing Sheets

(51) Int. Cl.
    *A61N 1/05*      (2006.01)
    *A61L 31/06*      (2006.01)
    *A61L 31/14*      (2006.01)
    *A61B 90/00*      (2016.01)
    *A61N 1/36*      (2006.01)
    *A61N 1/362*      (2006.01)
    *A61N 1/39*      (2006.01)

(52) U.S. Cl.
CPC ................ *A61L 31/14* (2013.01); *A61N 1/05* (2013.01); *A61B 2090/0807* (2016.02); *A61N 1/362* (2013.01); *A61N 1/3605* (2013.01); *A61N 1/3956* (2013.01)

(56) References Cited

U.S. PATENT DOCUMENTS

| | | |
|---|---|---|
| 5,746,722 A | 5/1998 | Pohndorf et al. |
| 2009/0125059 A1 | 5/2009 | Verzal et al. |
| 2011/0009935 A1 | 1/2011 | Kane et al. |

OTHER PUBLICATIONS

"Soluble and stable alternating main-chain merocyanine copolymers through quantitative spiropyran-merocyanine conversion" by Hartmut Komber, Stefan Mullers, Florian Lombeck. Alexander Held, Michael Walter and Michael Sommer; The Royal Society of Chemistry, Published on Aug. 22, 2013, Polym. Chem., 2014, 5, 443.

"Thermochromie, Piezochromie, Photochromie and Photomagnetismus" by Von Prof. Dr. G. Kortüm, Angew. Chem., 70. Jahrg. 1958 / Nr. 1.

German Search Report for German Case No. DE 10 2018 112 560.7, dated Jun. 29, 2018 (8 pages).

ELECTRODE FIXING SLEEVE WITH VISUAL FORCE INDICATOR

CROSS-REFERENCE TO RELATED APPLICATIONS

This patent application claims the benefit of and priority to co-pending German Patent Application No. DE 10 2018 112 560.7, filed on May 25, 2018 in the German Patent Office, which is hereby incorporated by reference in its entirety.

TECHNICAL FIELD

The present invention relates to a fixing device for fixing a longitudinally extended element, in particular in the form of an implantable electrode line, the electrode line also being called an electrode in the following.

BACKGROUND

With such fixing sleeves, surgical threads that are placed by the implanting physician are used, e.g., for fixing the sleeve to the electrode line. Threads used in this manner are also called ligature threads in the following.

U.S. Pat. No. 5,746,722 describes an electrode fixing sleeve in which a harder member of the sleeve prevents lacing for fixing the sleeve from being too tight and injuring the line. Moreover, U.S. Pat. No. 5,152,298 discloses an electrode fixing sleeve that comprises two parts, a sheathing and a collar, both having a thread, in which electrode fixing sleeve both parts fix the line when they are screwed together. Furthermore, International Publication No. WO 2015/48777 describes a micro-needle patch in which a mechanism may be used that makes it possible for the user to obtain feedback to support him in the correct and effective use of the micro-needle patch. The feedback may be provided in a number of forms or combinations, including visual feedback (e.g., changes in color).

There are inherent issues with the fixing sleeves identified above, which the present invention is directed at overcoming.

Proceeding from this, an underlying object of the present invention is to provide a fixing device having a fixing sleeve with which the user, in particular a physician, may adjust compression of the fixing sleeve by means of one or a plurality of fixing elements such that the fixing sleeve can satisfy the requirements for fixing the element to be fixed (e.g., an electrode) in the best possible manner. In particular it is desirable for the physician to be able to visually recognize compression of the fixing sleeve or tension on the fixing element that is too much or too little.

SUMMARY

At least this object is attained using a fixing device having the features of claim 1. Advantageous embodiments are given in the subordinate claims and shall be described in detail in the following.

According to claim 1, a fixing device is disclosed that has a fixing sleeve that surrounds an axially extended lumen for receiving the longitudinally extended element, the fixing sleeve having an inner side defining the lumen and an outer side facing away from the inner side, and the fixing sleeve being embodied, for fixing the fixing sleeve on the longitudinally extended element, to be compressed radially or to be subjected to compression by means of at least one fixing element.

According to the present invention, it is now provided that the fixing device, in particular the fixing sleeve, has an indicator device that is embodied to visually indicate to a user when a force applied to the fixing sleeve by means of the at least one fixing element for compressing the fixing sleeve attains or exceeds a threshold.

According to one embodiment, in this regard it may be provided that the fixing sleeve is embodied to change a visual appearance during compression, in particular using the compression-induced change in the geometric dimension of the fixing sleeve.

Moreover, according to one embodiment of the fixing device, it is provided that the fixing sleeve has at least one groove embodied in the outer side and extending along a circumferential direction of the fixing sleeve.

Furthermore, according to one embodiment of the fixing device, it is provided that the fixing device has at least one fixing element, or the at least one fixing element mentioned above, wherein the fixing element extends longitudinally and is embodied flexible and in particular pliable, and furthermore is designed and provided to be placed about the fixing sleeve in the groove, e.g., in the form of a loop, so that by means of the fixing element a force may be generated that leads to the compression of the fixing sleeve in the region of the groove. The fixing element may in particular be a so-called ligature thread. The at least one groove is correspondingly called a ligature groove.

Moreover, according to one embodiment, it is provided that the fixing sleeve is embodied, for fixing the fixing sleeve on the longitudinally extended element, to be subjected to radial compression by means of another fixing element. The indicator device in this case is in particular embodied to indicate visually when a force applied to the fixing sleeve by means of the other fixing element for compressing the fixing sleeve attains a threshold or exceeds a threshold.

According to one embodiment of the present invention, it is provided that the fixing sleeve has a further groove embodied in the outer side and extending along a circumferential direction of the fixing sleeve.

Moreover, according to one embodiment, the fixing device furthermore has a further fixing element, wherein the further fixing element extends longitudinally and is embodied flexible and in particular pliable, and is designed and provided to be placed in the other groove about the fixing sleeve, e.g., in the form of a loop, so that by means of the further fixing element a force may be generated that leads to the compression of the fixing sleeve in the region of the further groove. The fixing element may again in particular be a so-called ligature thread. The further groove is then correspondingly also called a ligature groove.

Using the compression of the fixing sleeve, the latter tightens about or presses against the aforesaid longitudinally extended element (e.g., electrode) running in the lumen of the fixing sleeve, so that the element or the electrode is fixed on the fixing sleeve.

Moreover, according to one embodiment of the fixing device, it is provided that the fixing sleeve has on the outer side an axially extended recess, in particular in the form of a through-hole to the lumen, in particular in the form of an elongated hole or gap, the recess extending from the groove to the further groove. The recess facilitates compression of the fixing sleeve by means of constriction by the fixing element and may in particular also act as a viewing window. During compression, a width of the recess may be reduced in the circumferential direction of the fixing sleeve due to deformation of the fixing sleeve.

In the following, for the sake of simplicity the possible embodiments of the indicator device shall each be described using the at least one groove. However, the indicator device may be embodied in the same manner with respect to the further groove (which may be present in all embodiments), i.e., in particular for the further groove the fixing device has corresponding features that are embodied identically to the features of the indicator device with respect to the other groove.

Moreover, according to one embodiment of the fixing device, it is provided that the fixing device is implantable, the fixing sleeve forming an electrode fixing sleeve that is embodied to fix a longitudinally extended element in the form of an implantable electrode in the body of the patient in an implanted state. The electrode may be the electrode of a medical implant (e.g., implantable pulse generator, in particular cardiac pacemaker, implantable cardioverter-defibrillator, or implantable neurostimulator).

Moreover, according to one embodiment of the fixing device, it is provided that the fixing sleeve is embodied transparent, at least section-wise or completely (image or visually transparent) or translucent (light-permeable) (in particular in the region of the indicator device and/or in the region of the at least one groove and/or in the region of the further groove.

Moreover, according to one embodiment of the fixing device, it is provided that the indicator device has, or is formed by, a material region connected to the fixing sleeve or a material region of the fixing sleeve, the material region having a piezochromic substance.

Moreover, according to one embodiment of the fixing device, it is provided that the material region is joined to the fixing sleeve in a positive fit and/or in a non-positive fit and/or in a material fit. If the material region is a material region of the fixing sleeve, this means that the material region is embodied integrally with the fixing sleeve, that is, e.g., is molded thereto.

Moreover, according to one embodiment of the fixing device, it is provided that the piezochromic substance is one of the following substances: a piezochromic polymer, a spiropyran, 1',3'-Dihydro-1',3',3'-trimethyl-6-nitrospiro[2H-1-benzopyran-2,2'-(2H)-indole].

Piezochromism is, e.g., a pressure-dependent equilibrium between two forms of the piezochromic substance (see Gustav Kortüm: "Thermochromie, Piezochromie, Photochromie und Photomagnetismus" [Thermochromy, Piezochromy, Photochromy, and Photomagnetism" in: Angewandte Chemie [Applied Chemistry], Volume 77, Nr. 1, 1958, pp. 14-20; Polym. Chem., 2014, 5, 443-453; Chemical Physics Letters: Volume 598, 8 Apr. 2014, pages 53-57), which is illustrated in the following using a spiropyran (SP) and the corresponding merocyanine (MC). The spiropyran may be colorless (transparent or translucent), while the MC produced by force molding (during compression of the fixing sleeve) may form a distinct color:

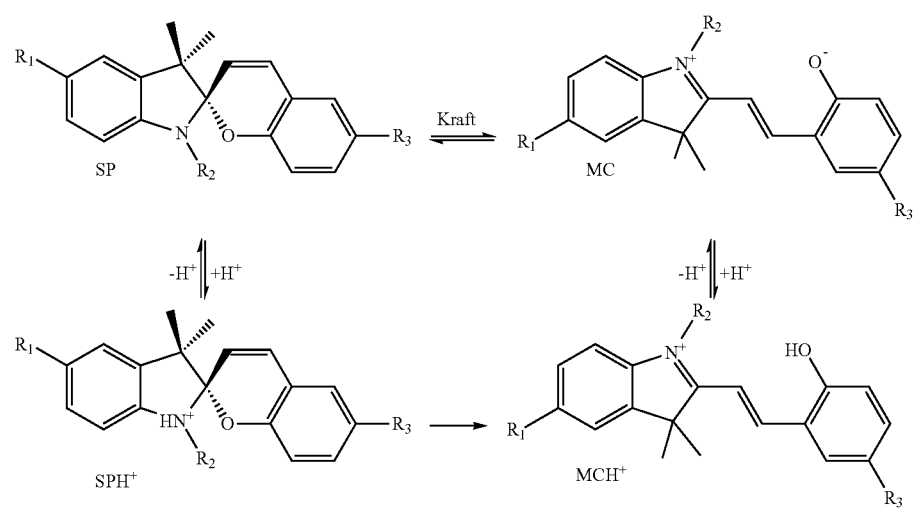

The fixing sleeve or the indicator device or material region is thus initially colorless or in a first color state and then changes to a second color state when a force exceeding the aforesaid threshold is exerted on the fixing sleeve or material region.

According to one embodiment of the fixing device, it may be provided that the fixing sleeve comprises one of the following substances: a thermoplastic polymer such as a polyether block amide block copolymer from the PEBAX® series by Arkema, the material types 6333, 3533, 7233, 3533, 4533, 5533 being preferred and PEBAX 6333 being particularly preferred. Likewise such as, e.g., polyurethane (PU) or a silicone rubber.

The aforesaid material region may be produced, e.g., according to one embodiment of the present invention, in that a spiropyran or merocyanine (for example, 1',3'-Dihydro-1',3',3'-trimethyl-6-nitrospiro[2H-1-benzopyran-2,2'-(2H)-indole]) is dissolved in a solvent (e.g., ethanol or tetrahydrofuran (THF) and is added to the material region or the fixing sleeve.

Moreover, according to one embodiment of the fixing device, it is provided that the material region is formed by a film. For example, according to one embodiment of the present invention, the spiropyran may be dissolved together with a thermoplastic (such as, e.g., Pellethane 55 D/55DE® from Lubrizol) and cast as a film. The material region is formed from the film produced in this manner and joined to the fixing sleeve, in particular by gluing.

Such exemplary embodiments thus provide, not that the entire fixing sleeve is provided with the piezochromic material (which, according to one embodiment, is also possible), but that only a region of the fixing sleeve that is clearly mechanically loaded (by the compression) is provided with the piezochromic material (e.g., in the area of the at least one fixing element or the at least one groove).

Moreover, according to one embodiment of the present invention, it is provided that the material region is arranged on the inner side of the fixing sleeve, and/or that the material region is arranged adjacent to the at least one groove, and/or that the material region is arranged radially below the at least one groove (that is, is opposite the at least one groove in the radial direction), and/or that the material region is arranged on the outer side of the fixing sleeve. The at least one groove thus encloses the material region.

According to one embodiment, the material region is embodied in a ring shape and/or in a band shape (e.g., an open ring shape). According to another embodiment, the material region extends in the circumferential direction of the fixing sleeve.

Moreover, according to one embodiment of the fixing device, it is provided that the material region has a greater hardness than the rest of the fixing sleeve.

According to one embodiment of the fixing device, it is provided that the hardness of the material region and/or the hardness of the rest of the fixing sleeve is a Shore hardness in the range of 10 A to 80 A or 25 D to 65 D. By adjusting the hardness, it is advantageously possible to adjust the force at which, i.e., the threshold at which, a change in color occurs.

Moreover, according to one embodiment of the fixing device, it is provided that the material region is embodied as a coating of the fixing sleeve.

In this regard, it is possible, e.g., to dissolve spiropyran/merocyanine in a solvent, PU, or other thermoplastics, such as a polyether block amide block copolymer from the PEBAX® series from Arkema, the material types 6333, 3533, 7233, 3533, 4533, 5533 being preferred and PEBAX 6333 being particularly preferred. Application is accomplished, for example, by coating, using a dipping process, or using a spraying process if the fixing sleeve comprises, e.g., PU, PEBAX®, or another thermoplastic as the base material.

Alternatively, a further layer of the fixing sleeve material (for example PU, PEBAX®, or silicone) may be applied over the layer. The further layer then acts as a protective layer for the layer.

Another embodiment having a material region embodied integrally with the fixing sleeve provides that the material region is produced in that the fixing sleeve, in this case produced, e.g., from PU, is treated with a solvent (for example, THF or dimethylsulfoxide (DMSO)) in the material region to be produced and the polychromatic substance, in particular spiropyran or merocyanine, is added in the treated region. Once the solvent has been removed, the piezochromic substance is bonded to the fixing sleeve.

Moreover, according to one embodiment of the fixing device, it is provided that the indicator device of the fixing device has an inner tube element that is arranged in the lumen of the fixing sleeve, as well as at least one inner groove of the fixing sleeve that is arranged adjacent to the at least one groove of the fixing sleeve and that has a matte surface. The inner groove may be arranged axially adjacent to the at least one groove or radially below the at least one groove. The aforesaid surface is configured to scatter light back to the user of the fixing device so that the surface may be differentiated for the user from an axially adjacent region of the fixing sleeve (in particular as a white ring) and wherein, if the force attains or exceeds the threshold, the surface is configured to press against or for its full surface to be positioned against the inner tube element such that the light can penetrate via the aforesaid surface into the inner tube element and the surface takes on a hue of the axially adjacent region of the fixing sleeve (and therefore the user can no longer differentiate it from the rest of the fixing sleeve). In other words, the user can no longer differentiate the color appearance of the surface from the color appearance of a surrounding or adjacent region of the fixing sleeve.

According to one embodiment of the present invention, the inner tube element may comprise a silicone, PU, PEBAX®, or other flexible thermoplastic polymer (e.g., a silicone tube element) that has a relatively smooth outer surface (for placing against the surface of the inner groove).

The at least one inner groove is produced, e.g., using a corresponding annular projection of a mold (e.g., injection molding mold) of the fixing sleeve. This annular projection on the mold in particular has a matte surface.

According to one embodiment of the present invention, it is provided that the at least one inner groove has a vent. The vent may be embodied, for example, in the form of a lateral through-hole of the fixing sleeve in the region of the inner groove. Fluid that is disposed between the fixing sleeve and electrode line may exit through the vent. This avoids the formation of a lubricating film on the surfaces of the electrode line and the fixing sleeve and thus prevents the fixing sleeve from sliding along the electrode line.

According to one embodiment of the present invention, it is furthermore provided that the inner tube element is a rigid tube element.

According to another embodiment of the present invention, it is provided that the inner tube element is formed by the longitudinally extended element or by the electrode to be fixed.

According to another embodiment, it is provided that the indicator device has a toothed inner surface that is formed by a section of the inner side of the fixing sleeve, which section is arranged radially preferably below or axially adjacent to the at least one groove, the toothed inner surface having a plurality of tooth flanks that are visible to a user from the outside of the fixing device (e.g., to the physician) as axially extended longitudinal stripes, the fixing sleeve being embodied to press the tooth flank against the longitudinally extended element (in particular an electrode) during the aforesaid compression, and an amount of force, in particular attainment of the threshold, being perceptible to the user in how far the tooth flanks are axially pressed against the longitudinally extended element, the indicator device furthermore in particular having a marking to the at least one groove that indicates when the threshold of the force has been attained.

One major advantage of this embodiment is that the operator/user may also see when he has securely tightened the fixing element or elements. Another advantage is that differences in diameter of the longitudinally extended element or electrode to be fixed may be compensated.

The toothed inner surface used in the foregoing may be produced, e.g., in that the core of the injection molding mold for the fixing sleeve is shaped like a wide toothed wheel, at least in the region about the at least one groove.

According to another embodiment of the present invention, it is provided that the indicator device has at least one hollow chamber embodied in the fixing sleeve, which hollow chamber is arranged adjacent to the at least one groove of the fixing sleeve (the hollow chamber may be arranged axially adjacent to the at least one groove or radially below the at least one groove, a dye being arranged in the hollow chamber and being embodied to distribute in the at least one hollow chamber at a desired compression of the fixing sleeve, or a dye in the form of at least one dye body, in particular in the form of a dye spherule or ring, containing at least one dye, being contained in the hollow chamber, and the dye body being destroyed when the force attains the threshold such that the dye is distributed in the at least one hollow chamber.

Due to the distribution of the dye in the hollow chamber, the dye takes on a large surface area axially or in the circumferential direction, and this is visible to the user. In this way it is possible to indicate to the user that a desired compression of the fixing sleeve or force for fixing the longitudinally extended element or the electrode has been attained.

According to one embodiment, the specific dye body has a membrane that may be destroyed by a force and that encloses the dye and that bursts or is destroyed upon desired compression of the fixing sleeve and releases the dye.

According to one embodiment of the present invention, the dye bodies or spherules may be produced in that an intense dye, such as, e.g., fluorescein or uranine, the water-soluble sodium salt of fluorescein, is added to an aqueous sodium alginate solution (3%). Small spherules of the sodium alginate/dye solution are added by drop to 8% calcium chloride solution, for example using a cannula. The size of the spherules may be adjusted using the blow-off air. The spherules are removed after a brief period of stirring (e.g., 30 seconds) and stored on filter paper. The strength of the membrane, on which strength the force for bursting depends, may be adjusted by the duration of the stirring time in $CaCl_2$. Due to the ionotropic gel formation, two $Na^+$ ions are replaced with one $Ca^{2+}$ ion. The three-dimensional network is created in this manner.

Moreover, the membrane for the specific dye body may be sprayed with a polymer in order to increase the strength. In this case the dye bodies are or may also be applied to the fixing sleeve and fixed there. If a UV lamp is used for illumination during the use of the fixing sleeve to which fluorescein has been added, the visual change, caused by compression of the fixing sleeve or force that acts on the fixing sleeve, is readily visible.

Fluorescein furthermore has the major advantage that, in addition to being readily detectable, it is also used and added as a contrasting agent in ophthalmology as an indicator. In the present invention, release of the indicator in particular is not intended. Unintentional release with the present dye would not be critical, however.

Moreover, according to one embodiment of the present invention, it is provided that the indicator device has at least one hollow chamber that is arranged in the fixing sleeve and to which a biocompatible dye (especially a viscous biocompatible dye) such as Dextran Blue (CAS Nr. 87915-38-6) is added, for example with a cannula. The fixing sleeve has an outlet opening that is in flow connection with the hollow chamber, the hollow chamber and the outlet opening being designed such that, if the force attains or exceeds the threshold, the dye exits from the hollow chamber through the outlet opening and is visible on the surface of the fixing sleeve, which in particular indicates that the desired compression or force is present. The outlet opening may be embodied in particular when the dye is added to the hollow body (e.g., using the cannula).

In another embodiment of the present invention, the indicator device may furthermore be produced for indicating compression or desired compression of the fixing sleeve made of materials having different deformation behavior, e.g., may be two parts combined, wherein scales, e.g., in the form of radially oriented, pronounced lines are added to the outer sides of the parts and in the starting position are not aligned. Due to compression, the inner part and/or the outer part and/or both parts deform such that the scales thereon are guided together.

According to another embodiment of the present invention, the indicator device may furthermore be embodied to use a prism effect or a total reflection for indicating compression or a desired compression of the fixing sleeve. To this end, the fixing sleeve or the material region is produced from at least to materials having different optical properties. In the non-loaded state only a portion of the light used during implantation, e.g., from the physician's head lamp, is reflected. When the fixing sleeve is compressed, the ratios of light refraction change and the angle of incidence reaches a certain magnitude, the refracted beams run parallel to the interface, and there is total reflection of the light. This optical effect may be utilized. It is also possible for there to be total reflection at the beginning and for it to change to partial reflection due to compression.

According to another embodiment of the present invention, the indicator device may furthermore have an illumination means, in particular in the form of an LED, that is actuated via a pressure sensor or two contacts, for displaying compression or a desired compression of the fixing sleeve. To this end, the fixing sleeve preferably comprises in its interior at least one LED, at least one galvanic element, and a pressure sensor or, as an alternative for the pressure sensor, two open lead ends. The at least one LED, the at least one galvanic element, and the pressure sensor or the open lead ends form an interrupted electric circuit. It is possible for the open lead ends of the electric circuit to contact if the fixing sleeve is compressed and the force required for compression attains or exceeds a threshold, this closing the electric circuit, and the LED illuminating. The LED illuminating is a visual signal that the threshold for compressing the fixing sleeve has been attained or exceeded.

According to another embodiment of the present invention, for displaying compression or a desired compression of the fixing sleeve, the indicator device may furthermore be made of a plastic that has a piezo effect (e.g., PVDF). By compressing the plastic, an electrical voltage is built up that may be used to permit current, e.g., for an LED, to flow.

Additional features, aspects, objects, advantages, and possible applications of the present invention will become apparent from a study of the exemplary embodiments and examples described below, in combination with the Figures, and the appended claims.

DESCRIPTION OF THE DRAWINGS

Additional features and embodiments of the present invention shall be explained in the following using the Figures.

DETAILED DESCRIPTION

Figure 1:
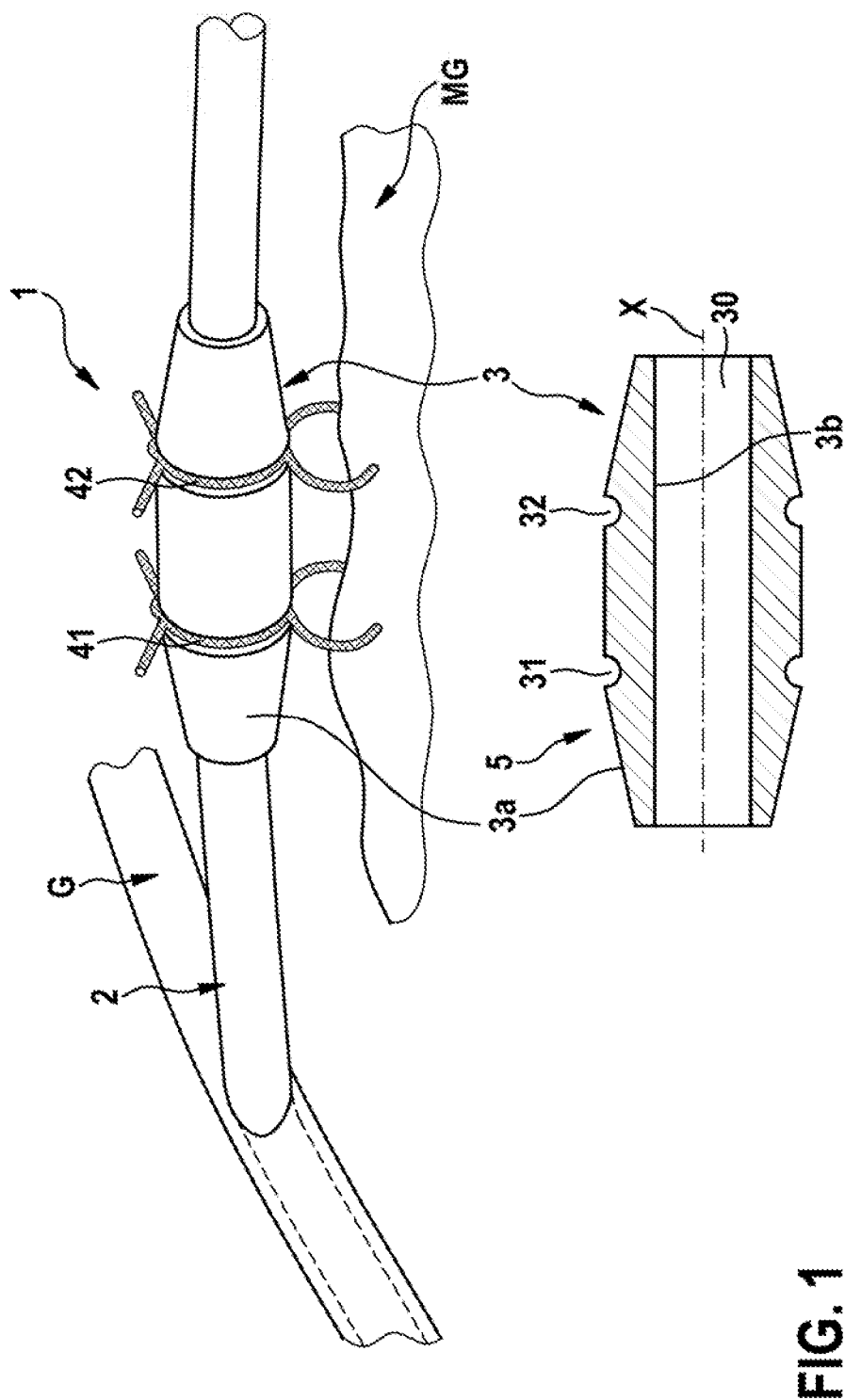
FIG. 1 depicts an embodiment of an inventive fixing device having a fixing sleeve for fixing a longitudinally extended element in the form of an electrode.

FIG. 1 depicts an embodiment of an inventive fixing device 1 having a fixing sleeve 3 for fixing a longitudinally extended element 2, in this case, for example, in the form of an implantable electrode 2. The electrode 2 has a longitudinally extended conduit body in which is arranged, in a known manner, at least one electrical lead (not shown here) that is in particular connected to an electrode contact that may be arranged on a surface of the conduit body in order to contact patient tissue. In the example in FIG. 1, the electrode 2 punctures a vessel G of the patient and is fixed via fixing elements 41, 42, which are fixed on the fixing sleeve 3 connected with muscle tissue MG of the patient. The fixing elements 41, 42 furthermore compress or constrict the fixing sleeve 3 such that the electrode 2 is securely clamped in a lumen 30 of the sleeve 3. The electrode 2 is positioned on an inner side 3b of the sleeve 3 (or on an inner tube element 51 of the sleeve 3, see below). According to the present invention, the device 1 has an indicator device 5 that is embodied to indicate visually when a force applied to the fixing sleeve 3 for compressing the fixing sleeve 3 by means of the fixing elements 41, 42 attains or exceeds a threshold. The fixing elements 41, 42 are placed about the sleeve 3 for exerting force in each of the grooves 31, 32 such that it is possible to constrict the sleeve by means of each fixing element 41, 42, which results in the sleeve 3 being compressed, at least in the region of each groove 31, 32, such that the electrode 2 is securely clamped in the lumen 30 of the sleeve 3.

The present invention shall be described using these two fixing elements 41, 42 in the following, the two associated grooves 31, 32 being spaced apart from one another in the axial direction x of the sleeve 3 and each running in a ring-like manner in the circumferential direction U of the sleeve 3 (see FIG. 2) on an outer side 3a of the sleeve 3. The two fixing elements 41, 42 are each preferably embodied as longitudinally extended and flexible elements that are preferably pliant. These elements may in particular be embodied as ligature threads 41, 42. However, it is also possible in the context of the present invention to use only one fixing element and one associated groove or to use more than two fixing elements/grooves. Other ideas for constriction are also possible.

Figure 2:
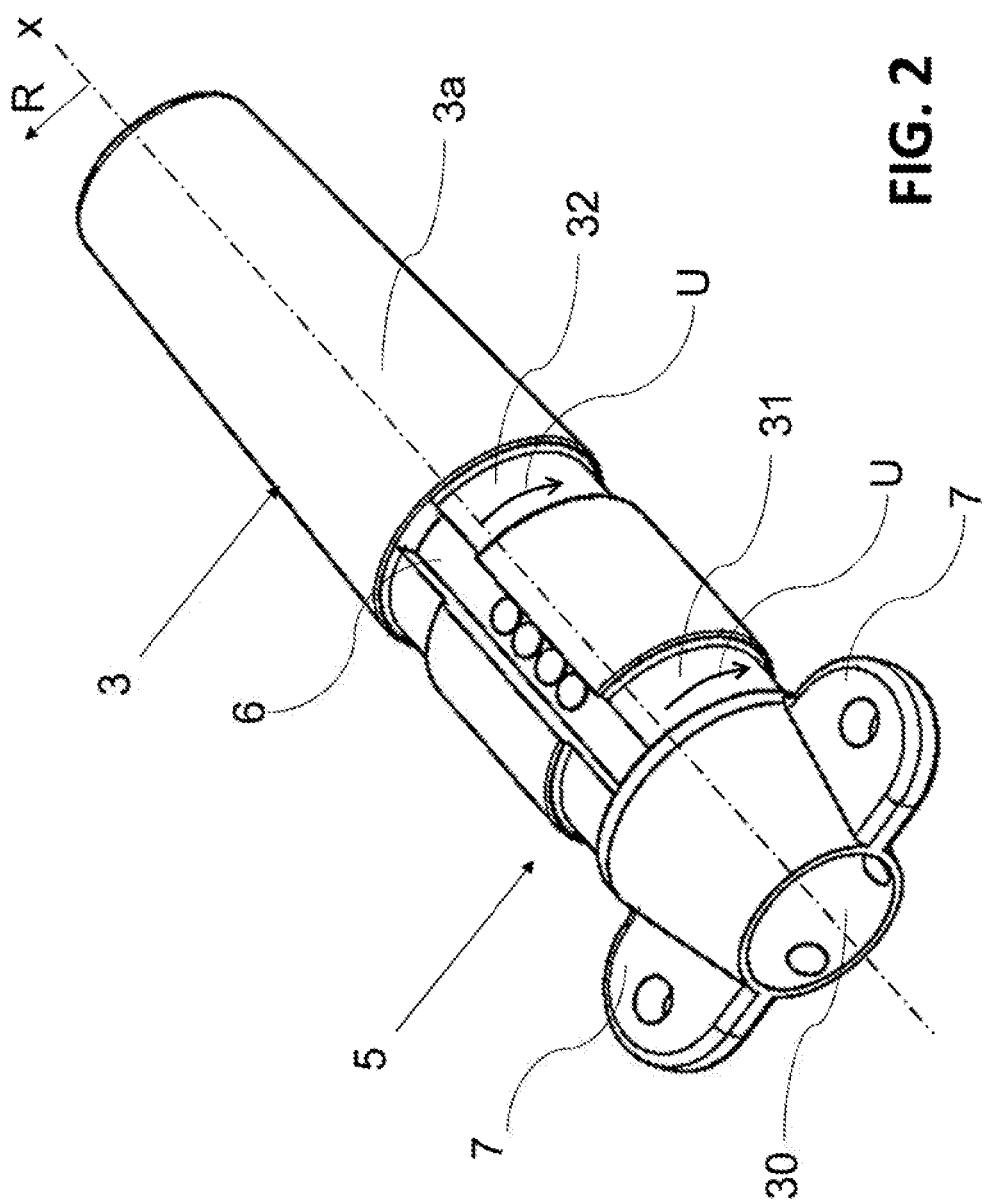
FIG. 2 is a perspective elevation of an embodiment of a fixing sleeve.

According to FIG. 2, the fixing sleeve 3 is preferably embodied at least translucent and may furthermore have a recess 6 extended in the axial direction x, extending between the two grooves 31, 32.

Moreover, the fixing sleeve 3 may have on one end (e.g., the distal or proximal end) wings 7, each having a through-hole via which the fixing sleeve may be secured, e.g., to bodily tissue.

FIGS. 3 through 8 depict possible embodiments of the indicator device 5 of the fixing sleeve 3, which may be embodied, e.g., as in FIG. 1 or 2. For the sake of simplicity, in FIGS. 3 through 8, the electrode 2 is not depicted (with the exception of FIG. 6). The electrode is arranged in the lumen 30 (as illustrated, e.g., in FIGS. 1 and 6) in order to be securely clamped there by the sleeve 3.

Figure 3:
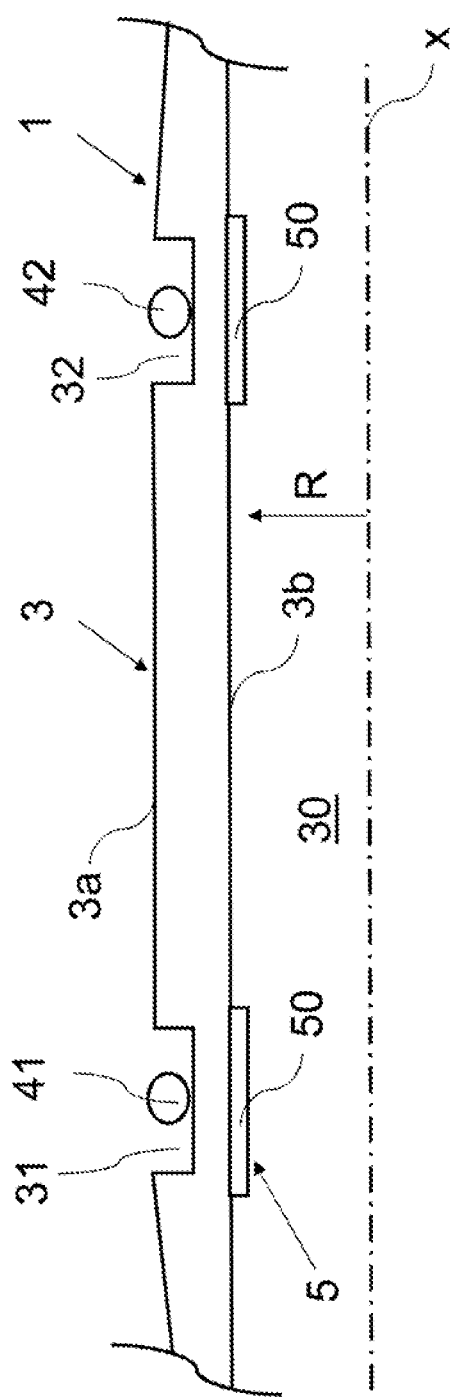
FIG. 3 is a partial schematic sectional depiction of an embodiment of an inventive fixing device having an indicator device that has material regions in the form of films that have a piezochromic substance.

According to FIG. 3, it is provided that the indicator device 5 has two material regions 50 that are joined to the fixing sleeve 3 and each of which may be, e.g., a film or a coating of the sleeve 3. The material regions 50 each have a piezochromic substance that may be, e.g., a piezochromic polymer, a spiropyran, in particular 1',3'-Dihydro-1',3',3'-trimethyl-6-nitrospiro[2H-1-benzopyran-2,2'-(2H)-indole]. The piezochromic substance may be added to the material region 50, e.g., in the manners described herein. According to FIG. 3, each material region 50 may be arranged on the inner side 3b of the fixing sleeve 3 in the lumen 30, specifically in the radial direction R below an associated groove 31 or 32. Other arrangements that permit deformation of the material regions 50 by the fixing elements 41, 42 are also possible. The material regions 50 may in particular have a greater hardness than the fixing sleeve 3, it being possible to adjust activation of the indicator device 5 using the selection of the hardness of the specific material region 50.

If the sleeve 3 is now radially compressed or constricted in the region of each of the grooves 31, 32, by the associated fixing element 41, 42, a corresponding force is exerted on each material region, wherein when a threshold is attained the piezochromic substance contained in each of the material regions changes color in a manner evident to the user and indicates to the user that the force necessary for fixing the electrode 2 has been attained.

Figure 4:
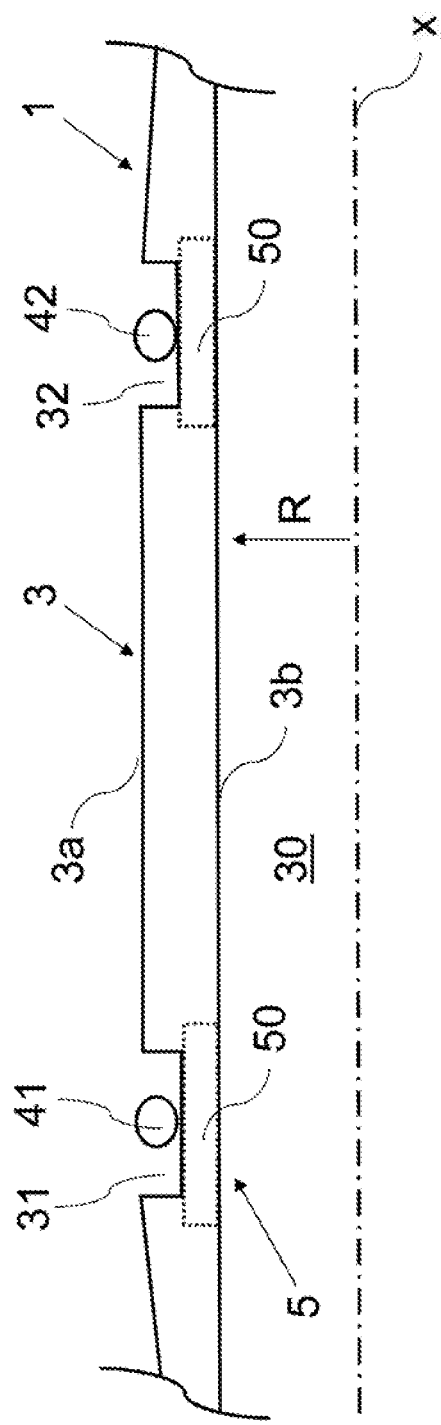
FIG. 4 is a partial schematic sectional depiction of an embodiment of an inventive fixing device, the material regions in this case being embodied integrally with the fixing sleeve.

According to FIG. 4, each material region 50 may also be embodied integrally with the fixing sleeve 3.

Figure 5:
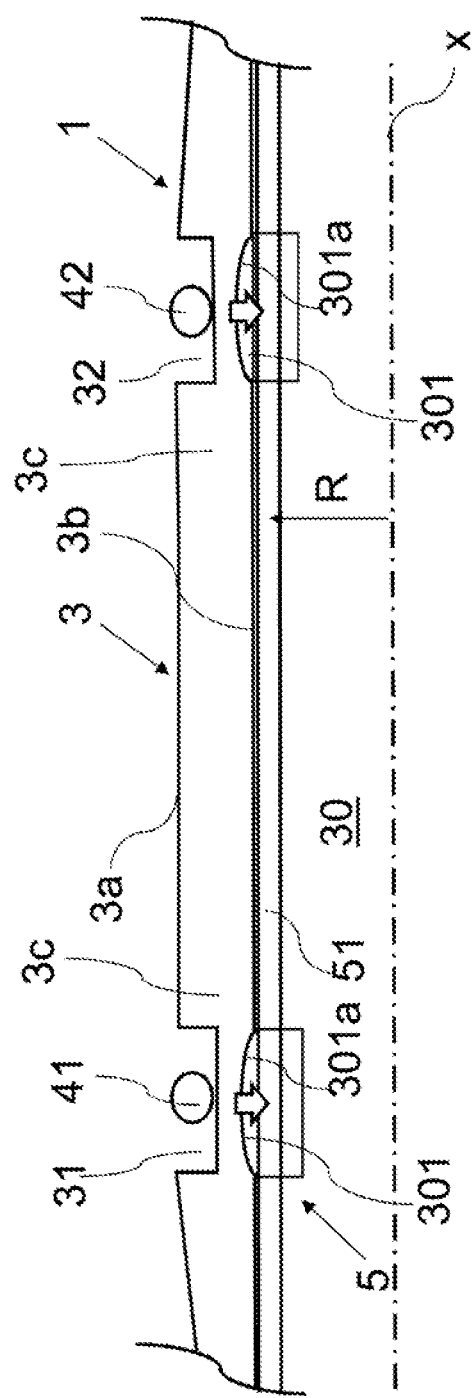
FIG. 5 is a partial schematic sectional depiction of an embodiment of an inventive fixing device, wherein in this case the indicator device has inner grooves that are provided on an inner side of the fixing sleeve and has an inner tube element that interacts with the inner grooves.

FIG. 5 depicts another embodiment of an inventive fixing device 1, in this case the indicator device 5 having an inner tube element 51 that is arranged in the lumen 30 of the translucent fixing sleeve 3 and having two inner grooves 301 that are embodied on the inner side 3b of the sleeve 3, each inner groove 301 being arranged in the radial direction R below an associated groove 31 or 32. The inner grooves 301 each have a matte surface 301a that is configured to scatter light back to the user (e.g., the physician) of the device 1 such that the user may differentiate the specific surface 301a from a region 3c of the sleeve 3 that is adjacent in the axial direction x (e.g., each in the form of a white ring). If the force exerted with the specific fixing element or compression of the sleeve 3 attains a pre-specified threshold, the surface area of the specific surface 301a is pressed against the inner tube element 51 such that the light is now coupled into the inner tube element 51 and the specific surface 301a takes on a hue that corresponds to the axially adjacent region 3c of the fixing sleeve 3. The user who is looking at the sleeve 3 from the outside can no longer differentiate the appearance of the color of the surfaces 301a from the appearance of the color of the adjacent region 3c and therefore knows that the required force has been attained. The inner tube element 51 may alternatively also be formed by the electrode 2.

Figure 6:
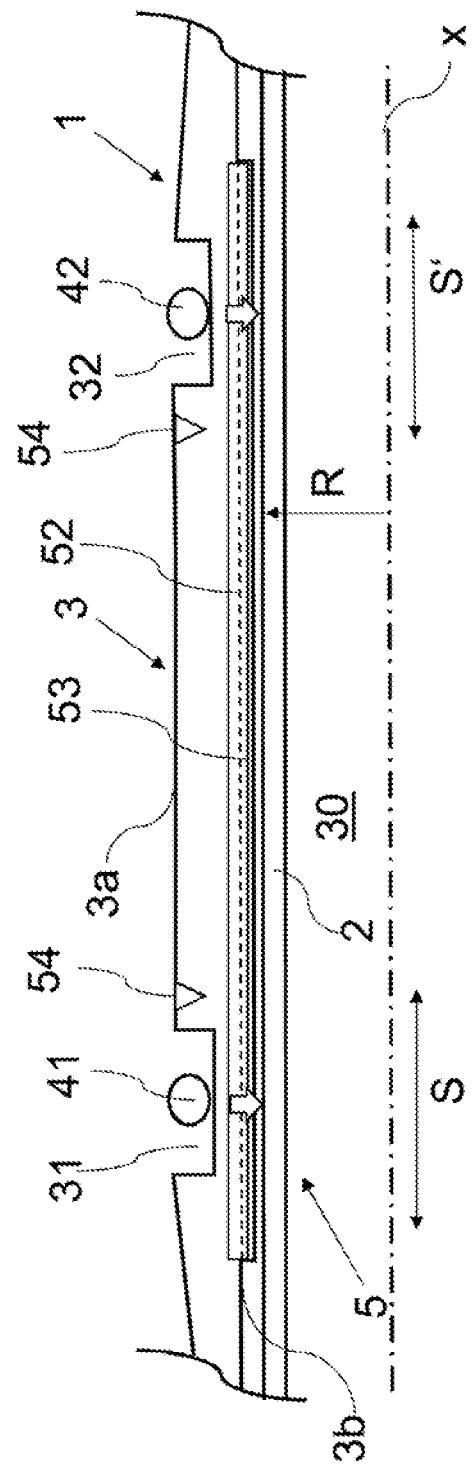
FIG. 6 is a partial schematic sectional depiction of an embodiment of an inventive fixing device, the indicator device having on an inner side of the fixing sleeve tooth flanks that interact with the electrode or the element to be fixed.

Moreover, FIG. 6 depicts one embodiment of an inventive device 1 in which the indicator device 5 has a toothed inner surface 52 that is formed by a section of the inner side 3b of the fixing sleeve 3, said section being arranged in the radial direction R below the grooves 31, 32, the toothed inner surface 52 having a plurality of tooth flanks 53, wherein the fixing sleeve 3 is embodied to press the toothed flanks 53 against the electrode 2 when there is radial compression caused by each of the fixing elements 41, 42, wherein an amount of the force, in particular attainment of the threshold is evident to the user by which section S, S' the toothed flanks 53 are pressed in the axial direction x against the longitudinally extended element 2. The indicator device 5 may furthermore have a marking 54 adjacent to each of the grooves 31, 32 that indicates when a predefined desired compression has been attained. FIG. 6 depicts as an example the situation of sufficient forces that have attained the threshold, since the sections S, S' each extend to the associated marking 54.

Figure 7:
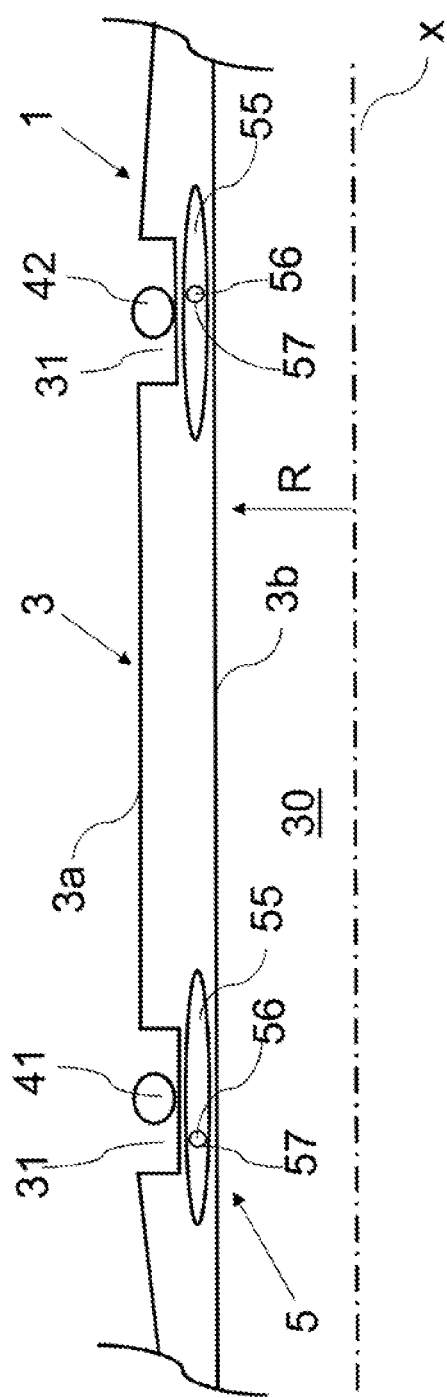
FIG. 7 is a partial schematic sectional depiction of an embodiment of an inventive fixing device, the indicator device having hollow chambers with a dye; and, FIG. 8 is a partial schematic sectional depiction of an embodiment of an inventive fixing device, in this case the indicator device having a dye that can exit from the fixing sleeve.

Furthermore, FIG. 7 depicts an embodiment of an inventive device 1 in which the indicator device 5 has two hollow chambers 55 embodied in the fixing sleeve 3, each hollow chamber 55 being arranged adjacent to an associated groove 31 or 32 of the fixing sleeve 3 so that each hollow chamber 55 is compressed when a force for clamping the electrode 2 is exerted via the associated fixing element 41, 42. Arranged in each hollow chamber 55 is a dye 56, in particular in the form of a dye body containing a dye 56, the membrane 57 of which surrounds the dye 56 and is destroyed when the force exerted by the specific fixing element 41, 42 for clamping the electrode 2 attains or exceeds the threshold and consequently flattens the associated hollow chamber 55 such that the associated membrane or shell 57 bursts and releases the dye 56 into the hollow chamber 55 so that it distributes there, which is readily visible to the user from outside.

Figure 8:
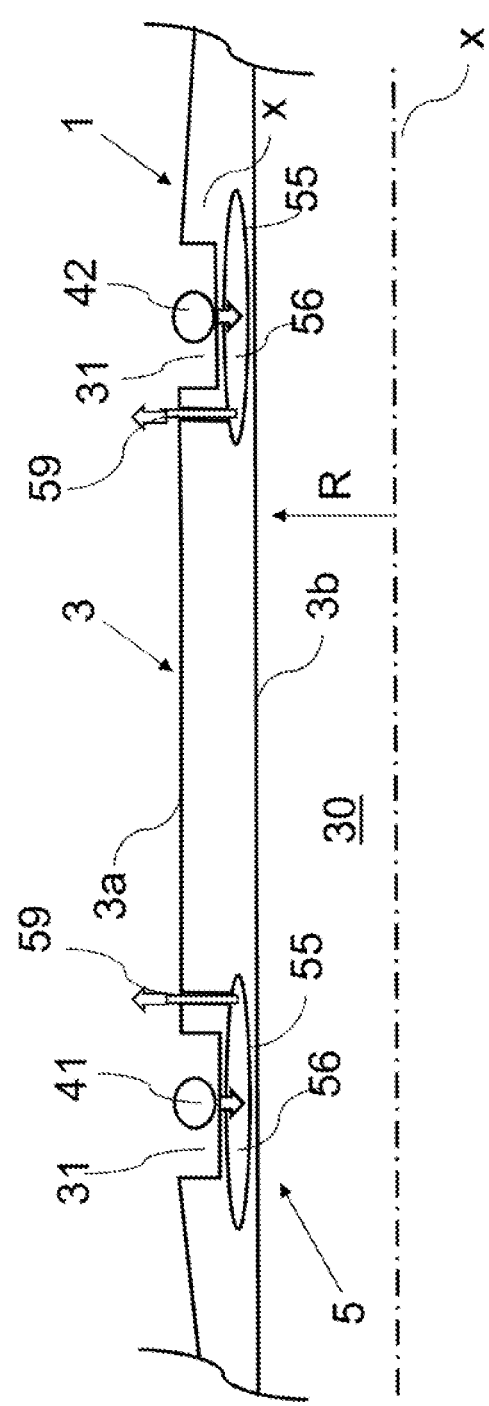

Furthermore, according to the embodiment depicted in FIG. 8, in contrast to FIG. 7, it is provided that a biocompatible dye 56 is arranged in the hollow chambers 55 and that it is pressed out of the associated hollow chamber 55 via outlet openings 59, which is also readily visible to the user, when the force exerted by the fixing element 41, 42 attains the threshold.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A fixing device for fixing a longitudinally extended element, the fixing device comprising:
 a fixing sleeve that surrounds a lumen extended in an axial direction for receiving the longitudinally extended element, the fixing sleeve having an inner side defining the lumen and an outer side facing away from the inner side, and the fixing sleeve being embodied for fixing the fixing sleeve on the longitudinally extended element, to be subjected to compression in the radial direction of the fixing sleeve by means of a fixing element, wherein the fixing device has an indicator device that is embodied to visually indicate when a force applied to the fixing sleeve by means of the fixing element for compressing the fixing sleeve attains or exceeds a threshold.

2. The fixing device according to claim 1, wherein the fixing sleeve has a groove embodied in the outer side and extending along a circumferential direction of the fixing sleeve.

3. The fixing device according to claim 1, wherein the fixing device has a longitudinally extended and flexible fixing element that is designed and provided to be placed about the fixing sleeve in the groove for applying the force.

4. The fixing device according to claim 1, wherein the fixing device is implantable, the fixing sleeve forming an electrode fixing sleeve that is embodied to fix a longitudinally extended element in the form of an implantable electrode.

5. The fixing device according to claim 1, wherein the fixing sleeve is embodied transparent.

6. The fixing device according to claim 1, wherein the indicator device has a material region joined to the fixing sleeve or has a material region of the fixing sleeve, the material region having a piezochromic substance.

7. The fixing device according to claim 6, wherein the piezochromic substance is one of the following substances: a piezochromic polymer, a spiropyran, 1',3'-Dihydro-1',3', 3'-trimethyl-6-nitrospiro[2H-1-benzopyran-2,2'-(2H)-indole].

8. The fixing device according to claim 6, wherein the material region is formed by a film.

9. The fixing device according to claim 6, wherein the material region is arranged at least one of:
 on the inner side of the fixing sleeve,
 in that the material region is arranged adjacent to the groove, and
 in that the material region is arranged below the groove in the radial direction.

10. The fixing device according to claim 6, wherein the material region has a greater hardness than the fixing sleeve, or in that the material region has a greater hardness than a region of the fixing sleeve adjacent to the material region.

11. The fixing device according to claim 6, wherein the material region is embodied as a coating of the fixing sleeve.

12. The fixing device according to claim 1, wherein the indicator device has an inner tube element that is arranged in the lumen of the fixing sleeve, as well as an inner groove arranged on the inner side of the fixing sleeve that is arranged adjacent to the groove of the fixing sleeve, the inner groove having a surface that is configured to scatter light back so that the surface may be differentiated for a user from a region of the fixing sleeve adjacent to the surface in the axial direction, and wherein, if the force attains or exceeds the threshold, the surface is configured to press against the inner tube element such that the light can penetrate via the surface into the inner tube element and the surface takes on a hue of the region of the fixing sleeve adjacent in the axial direction.

13. The fixing device according to claim 1, wherein the indicator device has a toothed inner surface that is formed by a section of the inner side of the fixing sleeve, which section is arranged below the groove in the radial direction, the toothed inner surface having a plurality of tooth flanks, the fixing sleeve being embodied to press the tooth flanks against the longitudinally extended element during the aforesaid compression, an amount of force being perceptible in how far the tooth flanks are pressed in the axial direction against the longitudinally extended element.

14. The fixing device according to claim 1, wherein the indicator device has a hollow chamber embodied in the fixing sleeve, which hollow chamber is arranged adjacent to the groove of the fixing sleeve, a dye being arranged in the hollow chamber and being embodied to distribute in the hollow chamber when the force attains or exceeds the threshold, or a dye in the form of a dye body containing a dye being contained in the hollow chamber, and the dye body being destroyed when the force attains or exceeds the threshold such that the dye is distributed in the hollow chamber.

15. The fixing device according to claim 1, wherein the indicator device has a hollow chamber that is arranged in the fixing sleeve and to which a biocompatible dye is added, wherein the fixing sleeve has an outlet opening that is in flow connection with the hollow chamber, the hollow chamber and the outlet opening being designed such that, if the force attains or exceeds the threshold, the dye exits from the hollow chamber through the outlet opening.

16. The fixing device according to claim 1, wherein the fixing sleeve is embodied translucent.

\* \* \* \* \*